United States Patent
Minato

(10) Patent No.: US 9,891,104 B2
(45) Date of Patent: Feb. 13, 2018

(54) SPECTROSCOPIC DETECTOR

(71) Applicant: SHIMADZU CORPORATION, Kyoto-shi, Kyoto (JP)

(72) Inventor: Hiroyuki Minato, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 15/204,418

(22) Filed: Jul. 7, 2016

(65) Prior Publication Data

US 2017/0010157 A1    Jan. 12, 2017

(30) Foreign Application Priority Data

Jul. 9, 2015  (JP) .................................. 2015-137743

(51) Int. Cl.
| | |
|---|---|
| *G01J 3/28* | (2006.01) |
| *G01J 3/18* | (2006.01) |
| *G01J 3/02* | (2006.01) |
| *G01J 3/10* | (2006.01) |
| G01N 30/74 | (2006.01) |

(52) U.S. Cl.
CPC .............. *G01J 3/18* (2013.01); *G01J 3/0291* (2013.01); *G01J 3/10* (2013.01); *G01N 30/74* (2013.01)

(58) Field of Classification Search
CPC ........ G01J 3/02; G01J 3/14; G01J 3/18; G01J 3/28; G01J 3/22; G01N 31/74
See application file for complete search history.

(56) References Cited

U.S. PATENT DOCUMENTS

| | | | | |
|---|---|---|---|---|
| 3,472,594 A | * | 10/1969 | Mavrodineanu ... | G01N 21/3103 356/320 |
| 4,647,202 A | * | 3/1987 | Kimura ................. | G01J 3/4406 250/458.1 |
| 2004/0051868 A1 | * | 3/2004 | Farr .......................... | G01J 3/14 356/326 |
| 2006/0001884 A1 | * | 1/2006 | Tani ..................... | G01N 21/553 356/445 |
| 2008/0285028 A1 | * | 11/2008 | Gunji ....................... | G01J 3/02 356/319 |

FOREIGN PATENT DOCUMENTS

JP    2008-256530 A    10/2008

* cited by examiner

*Primary Examiner* — Abdullahi Nur
(74) *Attorney, Agent, or Firm* — Westerman, Hattori, Daniels & Adrian

(57) ABSTRACT

Provided is a spectroscopic detector including: a light source for generating polychromatic light 11; a single diffraction grating 13; an excitation optical system for guiding the light from the light source 11 onto the diffraction grating 13, for selecting one wavelength from the light diffracted by the diffraction grating 13, and for casting the selected wavelength of light into a sample as excitation light; a detection optical system for guiding observation light emitted from the sample irradiated with the excitation light onto the diffraction grating 13 to disperse the observation light; and a photodetector 15 for detecting the observation light dispersed by the detection optical system. By using one diffraction grating 13 in both the excitation optical system and the detection optical system, the number of diffraction gratings is reduced, whereby both the cost reduction and the downsizing of the device are achieved.

4 Claims, 2 Drawing Sheets

TOP VIEW

FRONT VIEW

SPECTROSCOPIC DETECTOR

TECHNICAL FIELD

The present invention relates to a spectroscopic detector for irradiating a sample with a specific wavelength of excitation light, for dispersing observation light emitted from the sample, such as fluorescence or Raman light, and for detecting the dispersed light. For example, such a spectroscopic detector is used for analyzing a sample eluted from a column in a liquid chromatograph.

BACKGROUND ART

Conventionally, spectroscopic detectors have been used for an analysis of a sample which enters a flow cell after being doted from a column in a liquid chromatograph (see Patent Literature 1).

FIG. 4A is a top view of a spectroscopic detector 90 described in Patent Literature 1, and FIG. 4B is a front view of the same detector. In this spectroscopic detector 90, as shown in FIG. 4A, polychromatic light is generated from a light source 91, which includes a xenon lamp. After being reflected by an excitation light mirror 921, this light passes through a slit 961 and falls onto the surface of an excitation light diffraction grating 931, which disperses the light into a spectrum. From among this spectrum of light, a specific wavelength of light passes through a slit 94 and enters the flow cell C as the excitation light. The sample in the cell C is irradiated with this excitation light and emits observation light. The rotatable excitation light diffraction grating 931 is rotatable. By turning this grating 931, the wavelength of the excitation light which is extracted from the polychromatic light of the light source 91 and introduced into the flow cell C, is changed according to the kind of sample to be analyzed.

As shown in FIG. 4B, the observation light generated from the sample is reflected by a mirror (not shown) placed within the flow cell C, to be extracted through the exit window W to the outside of the flow cell C. After being reflected by an observation light mirror 922, the light passes through a slit 962 and falls onto the surface of an observation light diffraction grating 932, which disperses the light into a spectrum. By turning the observation light diffraction grating 932, the amount of light at each wavelength within the spectrum can he detected with a photodetector 95. As the photodetector 95, for example, a photodiode array or photomultiplier tube is used. It should be noted that, for an easy view of the optical system, the observation light mirror 922 and the observation light diffraction grating 932 are omitted from FIG. 4A, while the excitation light mirror 921, the excitation light diffraction grating 931 and the slit 94 are omitted from FIG. 4B.

CITATION LIST

Patent literature

Patent Literature 1 : JP 2008-256530 A

SUMMARY OF INVENTION

Technical Problem

As just described, two diffraction gratings are used in the spectroscopic detector disclosed in Patent Literature 1. A diffraction grating is an expensive optical element that requires a high-precision working process in its manufacturing. Using two such diffraction gratings inevitably increases the cost of the spectroscopic detector. Additionally, using a larger number of optical elements increases the size of the entire optical system, which eventually leads to an increase in the entire size of the spectroscopic detector.

The problem to be solved by the present invention is to provide a spectroscopic detector which requires fewer diffraction gratings and thereby allows for both the cost reduction and the downsizing of the device.

Solution to Problem

The spectroscopic detector according to the present invention developed for solving the previously described problem includes:

a) a light source for generating polychromatic light;
b) a single diffraction grating;
c) an excitation optical system for guiding the light from the light source onto the diffraction grating, for selecting one wavelength from the light diffracted by the diffraction grating, and for casting the selected wavelength of light into a sample as excitation light;
d) a detection optical system for guiding observation light emitted from the sample irradiated with the excitation light onto the diffraction grating to disperse the observation light; and
e) a photodetector for detecting the observation light dispersed by the detection optical system.

In the spectroscopic detector according to the present invention, one diffraction grating is commonly used in both the excitation optical system and the detection optical system. Accordingly, the number of diffraction gratings used is only one, which is fewer than the conventional number. Therefore, the cost incurred by the diffraction grating is reduced. Furthermore, the entire optical system including the excitation and detection optical systems can be smaller in size, so that the spectroscopic detector can also be downsized.

In the spectroscopic detector according to the present invention, it is preferable to provide a difference in position between the plane of incidence of the excitation light and the plane of incidence of the observation light on the diffraction grating. According to this configuration, the two spectrums produced by the diffraction of the two rays of light, i.e. the excitation light and the observation light incident on the diffraction grating, are formed at different positions, whereby the excitation light is prevented from becoming stray light and entering the photodetector.

The spectroscopic detector according to the present invention may further include: a grating driver for turning the diffraction grating; and a photodetector driver for moving the photodetector to the position where diffracted light of the observation light which moves with the turning of the diffraction grating is introduced into the photodetector. According to this configuration, it is possible to turn the diffraction grating in order to change the wavelength of the excitation light cast into the sample, while making the diffracted light of the observation light, which moves with the turning operation, be correctly introduced into the photodetector. However, it is unnecessary to provide the grating driver and photodetector driver in the case where the wavelength of the excitation light cast into the sample is fixed, as in the case of repeatedly performing a measurement for samples which contain the same target component.

Advantageous Effects of the Invention

According to the present invention, it is possible to decrease the number of diffraction gratings used in a spectroscopic detector to only one and thereby allow for both the cost reduction and the downsizing of the device.

DESCRIPTION OF EMBODIMENTS

Figure 1:
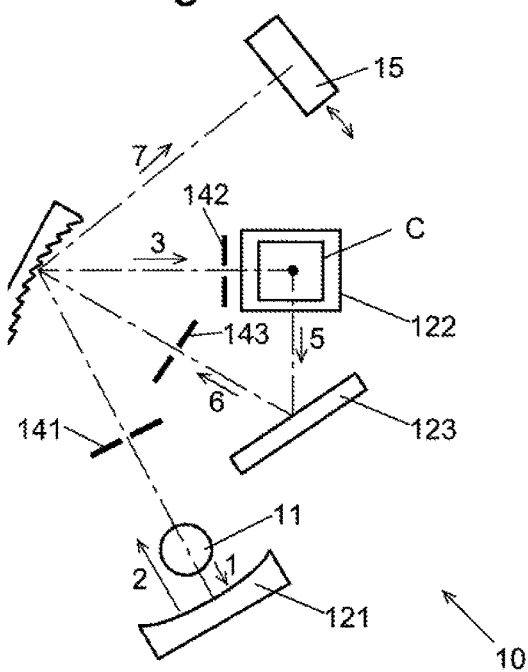
FIG. 1 is a top view showing one embodiment of the spectroscopic detector according to the present invention.
Figure 2:
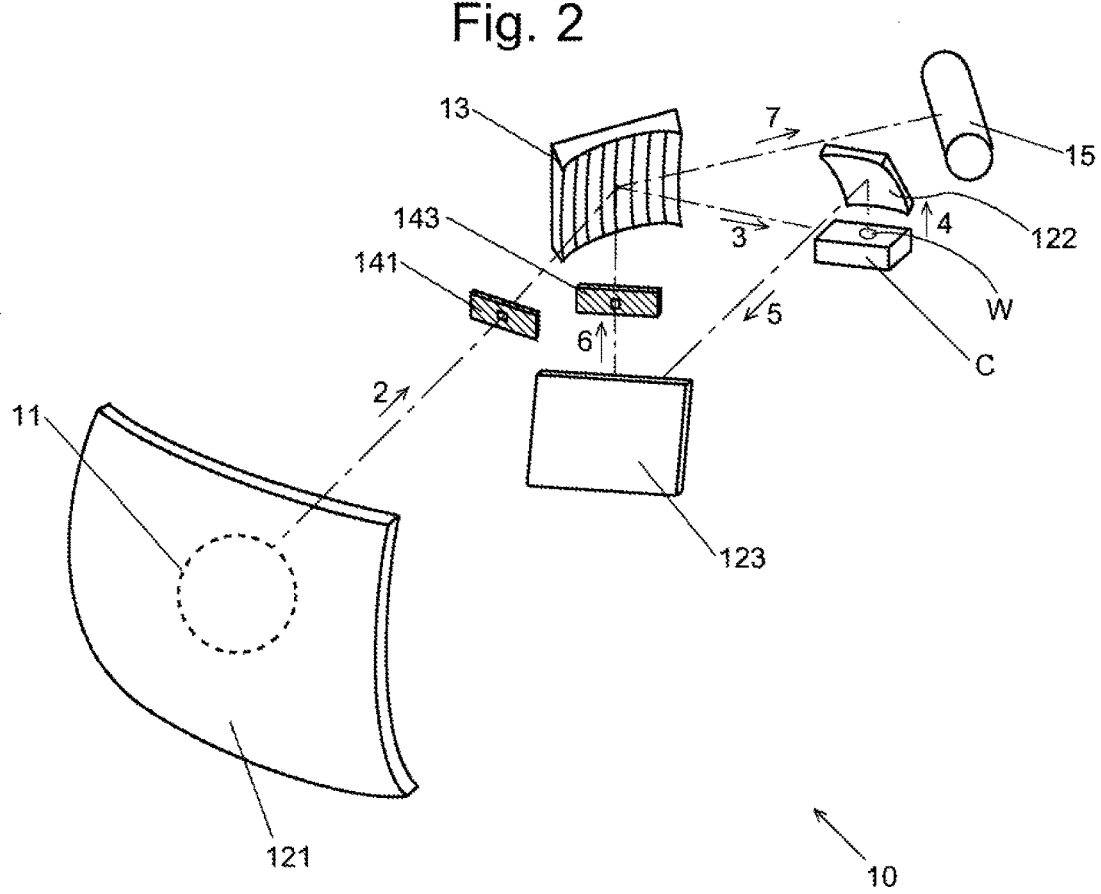
FIG. 2 is a perspective view showing a schematic configuration of the spectroscopic detector of the present embodiment.
Figure 3:
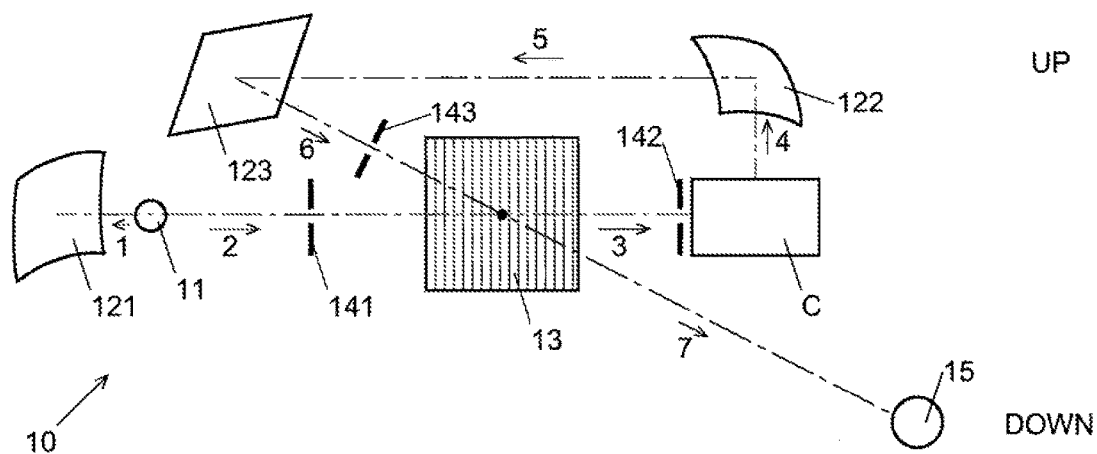
FIG. 3 is a model diagram showing the vertical positional relationship of the components in the spectroscopic detector of the present embodiment.
Figure 4A:
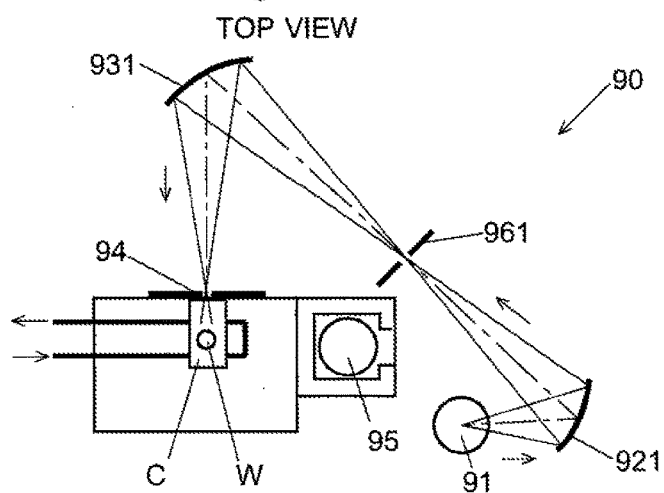
FIGS. 4A and 4B are schematic configuration diagrams showing one example of the conventional spectroscopic detector.
Figure 4B:
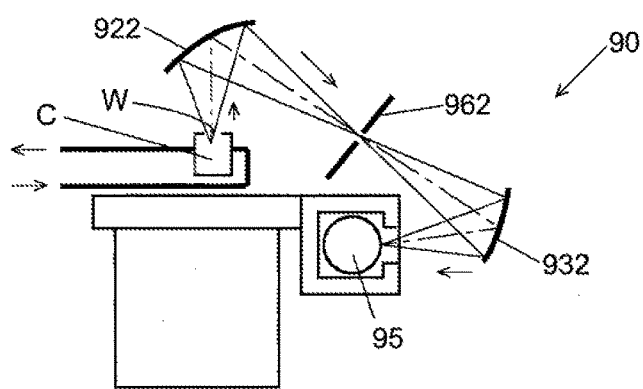

One embodiment of the spectroscopic detector according to the present invention is hereinafter described using FIGS. 1-3. It should be noted that FIG. 3 mainly shows the vertical positional relationship of the components; other aspects of those components are omitted or simplified, such as their individual shapes or their positional relationship in the depth direction.

The spectroscopic detector 10 of the present embodiment is configured to analyze a sample flowing into a flow cell C. The spectroscopic detector 10 includes a light source 11, first through third mirrors 121-123, a diffraction grating 13, first through third slits 141-143 and a photodetector 15. Each of these components is hereinafter described.

The light source 11 generates polychromatic light. In the present embodiment, a xenon lamp is used. Xenon lamps generate polychromatic light having a continuous spectrum over a broad range of wavelengths from ultraviolet through infrared regions. Xenon lamps are a point source and spherically radiate light.

The first mirror 121 is a concave mirror, which collects the polychromatic light from the light source 11 and reflects it onto the surface of the diffraction grating 13. The first slit 141 is located between the first mirror 121 and the diffraction grating 13, at the position on which the polychromatic light reflected by the first mirror 121 is focused. The diffraction grating 13 is a concave grating, which is placed at such a position where the entire grating surface is illuminated by the spreading polychromatic light which has passed through the first slit 141. In the present embodiment, the axis of the polychromatic beam extending from the first mirror 121 through the first slit 141 to the diffraction grating 13 (indicated by the chain line in FIGS. 1 and 3) is assumed to be substantially horizontal, although the present invention is not limited to this arrangement. The diffraction grating 13 has grooves which vertically extend at the position where the beam axis of the polychromatic light intersects with the grating surface (accordingly, those grooves are perpendicular to the beam axis of the polychromatic light). The diffraction grating 13 is rotatable about a vertical axis. The beam axis of the polychromatic light intersects with this vertical axis on the grating surface.

The flow cell C is placed in such a manner that its entrance window (not shown) for allowing the incidence of the excitation light is located on a substantially horizontal optical axis which makes a predetermined angle with the optical axis which extends from the first mirror 121 to the diffraction grating 13. By turning the diffraction grating 13 about the vertical axis in the previously described manner, a specific wavelength of light within the spectrum of the polychromatic light can be selected as the excitation light to be introduced into the entrance window of the flow cell C. Since the diffraction grating 13 is a concave grating, it is possible to focus the excitation light on the sample within the flow cell C by appropriately setting the distance between the diffraction grating 13 and the flow cell C. Immediately before the entrance window of the flow cell C, the second slit 142 (not shown in FIG. 2) is placed.

The flow cell C has an exit window W on its upper side. The observation light (e.g. fluorescence) emitted from the sample irradiated with the excitation light is extracted through this exit window W to the outside of the flow cell C. Located immediately above the exit window W (see FIGS. 2 and 3) is the second mirror 122, which is a concave mirror arranged so as to receive the observation light extracted from the exit window W and reflect it in a substantially horizontal direction. On the optical axis for the observation light reflected by the second mirror 122, the third mirror 123 is provided. The third mirror 123 is oriented so that the optical axis for the observation light coming from the second mirror 122 is redirected by the third mirror 123 to an obliquely downward direction leading to the diffraction grating 13. Accordingly, all wavelength components of the observation light diffracted by the diffraction grating 13 have obliquely downward beam axes lying in one plane together with the beam axis of the observation light incident on the diffraction grating 13, although the direction of the beam axis changes with the wavelength. Additionally, on the optical path between the second mirror 122 and the diffraction grating 13, the third slit 143 is placed at the position on which the observation light is focused by the second mirror 122. It should be noted that the arrangement of the optical elements in the present configuration may be changed so that both the optical axis extending from the third mirror 123 to the diffraction grating 13 and the optical axis extending from the first mirror 121 to the diffraction grating 13 lie in the same vertical plane (a plane perpendicular to the plane of FIG. 1).

The photodetector 15 used in the present embodiment includes a photomultiplier tube, which is moveable in the plane in which the aforementioned beam axes of the wavelength components of the diffracted observation light lie. Making the photodetector 15 movable in this plane is aimed at detecting the diffracted observation light at each wavelength with the photomultiplier tube as well as adjusting the position of the photodetector 15 to the beam axis of the diffracted observation light whose position changes when the diffraction grating 13 is turned so as to set the wavelength of the excitation light.

Among the previously described components, the first mirror 121, first slit 141, diffraction grating 13 and second slit 142 constitute the excitation optical system, while the second mirror 122, third mirror 123, third slit 143 and diffraction grating 13 constitute the detection optical system. In other words, the diffraction grating 13 is commonly used in both excitation and detection optical systems.

The spectroscopic detector 10 of the present embodiment operates as follows:

The polychromatic light generated by the light source 11 is collected and reflected by the first mirror 121 consisting of the concave mirror. The reflected light passes through the first slit 141 and falls onto the diffraction grating 13. The diffraction grating 13 diffracts the polychromatic light into a spectrum containing a range of wavelengths of light travelling in different directions. Only a specific wavelength of light diffracted toward the second slit 142 is selectively allowed to pass through this slit 142 and be introduced into the flow cell C.

The excitation light having the aforementioned wavelength is cast into the sample flowing into the flow cell C, causing the sample to emit observation light (e.g. fluorescence). The observation light travelling upward exits through the exit window W to the outside of the cell C. Subsequently, the observation light hits the second mirror 122 above the flow cell C and is thereby reflected in as substantially horizontal direction. After being reflected obliquely downward by the third mirror 123, the observation light passes through the third slit 143 and falls onto the diffraction grating 13, with its beam axis directed obliquely downward. The diffraction grating 13 disperses the observation light into a spectrum containing a range of wavelengths of light, which further travel obliquely downward in different directions. The photodetector 15 detects the amount of light at each wavelength of the diffracted observation light.

When the wavelength of the excitation light cast into the sample needs to be changed, the diffraction grating 13 is turned in the previously described manner so as to change the wavelength of the light diffracted toward the second slit 142.

The spectroscopic detector 10 of the present embodiment uses only a single diffraction grating. Therefore, it is possible to make the device less expensive and smaller in size than the conventional spectroscopic detector.

Both the incident light falling onto the diffraction grating 13 and the diffracted light produced by the diffraction grating 13 have substantially horizontal beam axes. The plane of incidence of the excitation light onto the diffraction grating 13 is also substantially horizontal. On the other hand, the plane of incidence of the observation light onto the diffraction grating 13 is inclined from the horizontal plane. By providing such a difference in the position between the plane of incidence of the excitation light and that of the observation light, the excitation light is prevented from entering the photodetector 15 as stray light.

The present invention is not limited to the previous embodiment. The configuration of the spectroscopic detector can be appropriately changed within the spirit of the present invention.

REFERENCE SIGNS LIST 10, 90 . . . Spectroscopic Detector
11, 91 . . . Light Source
121 . . . First Mirror
122 . . . Second Mirror
123 . . . Third Mirror
13 . . . Diffraction Grating
141 . . . First Slit
142 . . . Second Slit
143 . . . Third Slit
15, 95 . . . Photodetector
921 . . . Excitation Light Mirror
922 . . . Observation Light Mirror
931 . . . Excitation Light Diffraction Grating
932 . . . Observation Light Diffraction Grating
94, 961, 962 . . . Slit
C . . . Flow Cell
W . . . Exit Window

The invention claimed is:

1. A spectroscopic detector, comprising:
a) a light source for generating polychromatic light;
b) an excitation optical system,
c) an detection optical system,
d) a single diffraction grating configured to be used in both the excitation optical system and the detection optical system, wherein:
e) the excitation optical system is configured to guide the light from the light source onto the diffraction grating, is configured to select one wavelength from the light diffracted by the diffraction grating, and is configured to cast the selected wavelength of light into a sample as excitation light, and
f) the detection optical system is configured to guide observation light emitted from the sample irradiated with the excitation light onto the diffraction grating to disperse the observation light; and
g) a photodetector for detecting the observation light dispersed by the detection optical system,
wherein the excitation optical system comprises:
a first mirror arranged to collect and reflect light from the light source;
a first slit arranged to pass through the light reflected by the first mirror; and
a second slit arranged to pass through a specific wavelength of light diffracted by the single diffraction grating as the excitation light, and
wherein the detection optical system comprises:
a second mirror arranged to reflect the observation light
a third mirror arranged to reflect the observation light reflected by the second mirror; and
a third slit arranged to pass through the observation light reflected by the third mirror.

2. The spectroscopic detector according to claim 1, wherein there is a difference in position between a plane of incidence of the excitation light and a plane of incidence of the observation light on the diffraction grating.

3. The spectroscopic detector according to claim 1, further comprising:
a grating driver for turning the diffraction grating; and
a photodetector driver for moving the photodetector to a position where diffracted light of the observation light which moves with the turning of the diffraction grating is introduced into the photodetector.

4. The spectroscopic detector according to claim 2, further comprising:
a grating driver for turning the diffraction grating; and
a photodetector driver for moving the photodetector to a position where diffracted light of the observation light which moves with the turning of the diffraction grating is introduced into the photodetector.

* * * * *